United States Patent [19]

Fawzi

[11] Patent Number: 4,497,744
[45] Date of Patent: Feb. 5, 1985

[54] GENTISIC ACID SALTS AS RADIOGRAPHIC SCANNING AGENT STABILIZERS

[75] Inventor: Mahdi B. Fawzi, Cincinnati, Ohio

[73] Assignee: Mallinckrodt, Inc., St. Louis, Mo.

[21] Appl. No.: 202,962

[22] Filed: Nov. 3, 1980

Related U.S. Application Data

[62] Division of Ser. No. 892,245, Mar. 31, 1978, Pat. No. 4,233,284.

[51] Int. Cl.$^3$ ................................................ C07F 7/22
[52] U.S. Cl. .......................... 260/429.7; 260/438.5 R; 424/1.1
[58] Field of Search .......... 260/429.7, 439 R, 438.5 R

[56] References Cited

U.S. PATENT DOCUMENTS 3,673,157  6/1972  Price et al. ................. 260/429 R X

OTHER PUBLICATIONS

Fenton et al., Inorganica Chimica Acta, 4, 235–243, (1970).
Honnick et al., Inorganic Chemistry, 17, 501–504, (1978).
Chemical Abstracts, vol. 54, 19259a, (1960).
Chemical Abstracts, vol. 79: 35670b, (1973).

Primary Examiner—Helen M. S. Sneed
Attorney, Agent, or Firm—Bernard, Rothwell & Brown

[57] ABSTRACT

Stable compositions, useful as technetium-99m-based scintigraphic agents, comprise gentisic acid or a pharmaceutically-acceptable salt or ester thereof in combination with a pertechnetate reducing agent or dissolved in pertechnetate-99m ($^{99m}TcO_4^-$) solution. The compositions are especially useful in combination with a phosphate or phosphonate material which carries the radionuclide to bone, thus providing a skeletal imaging agent.

2 Claims, No Drawings

GENTISIC ACID SALTS AS RADIOGRAPHIC SCANNING AGENT STABILIZERS

This is a division of application Ser. No. 892,245, filed Mar. 31, 1978 now U.S. Pat. No. 4,233,284.

BACKGROUND OF THE INVENTION

This invention relates to compositions useful in the preparation of stable scintigraphic scanning (or, "radiodiagnostic") agents employing technetium-99m. More particularly, gentisic acid (or soluble gentisate compound) is used as a non-interfering stabilizer for such compositions.

Scintigraphy and similar radiographic techniques are finding ever increasing application in biological and medical research and diagnostic procedures. In general, scintigraphy procedures involve the preparation of radioactive scanning agents which, upon introduction into a biological subject, become localized in specific organs, tissue or skeletal material which are under study. When so localized, traces, plots or scintiphotos of the distribution of the radioactive material can be made by various radiation detectors, i.e., such as traversing scanners, scintillation cameras and the like. The resultant distribution and corresponding relative intensities can then be used to indicate the position occupied by the tissue in which the radionuclide is localized as well as indicate the presence of aberrations, pathological conditions, and the like.

In general, and depending on the type of radionuclide used and the organ of interest, a scintigraphic scanning agent as used in the hospital comprises a radionuclide, a carrier agent designed to target the specific organ, various auxiliary agents which affix the radionuclide to the carrier, water or other delivery vehicle suitable for injection into, or aspiration by, the patient, physiologic buffers and salts, and the like.

Technetium-99m is a radionuclide which is widely known for use in tissue scanning agents. This radionuclide is conveniently available from commercial pertechnetate sources.

Pertechnetate is in the +7 oxidation state, which is too high to be used in the preparation of scanning agents such as those used for bone mineral and lung. This problem is easily overcome by reducing the pertechnetate to what is believed to be the +3, +4 and/or +5 oxidation state.

In general, $^{99m}$Tc-labeled scanning agents are prepared by admixing a pertechnetate-99m isotonic saline solution with a pertechnetate reducing agent such as the stannous, ferrous or chromous salt of sulfuric or hydrochloric acid, and the desired carrier agent for targeting the organ of interest. For example, U.S. Pat. No. 3,983,227, Tofe and Francis, discloses the use of reducing salts with radioactive pertechnetate solutions and organophosphonate bone-seeking carriers to prepare bone scanning agents. U.S. Pat. No. 4,002,730, Tofe, Hartman and Kretschmar, describes $^{99m}$Tc lung scanning agents prepared by mixing a pertechnetate solution from commercial generators with stannous/starch particles which provide a combined reducing agent/carrier.

While such procedures provide scanning agents which are superior to those previously available, they have shortcomings. Most notably, it has been found that conventional technetium-containing scintigraphic scanning agents are unstable in the presence of oxygen and radiolysis products. Accordingly, previously-described technetium-based scanning agents have been made oxygen-free by saturating the composition with oxygen-free nitrogen gas or by preparing the agent is an oxygen-free atmosphere or in a vacuum. However, even such painstaking precautionary procedures are not entirely satisfactory, since it is extremely difficult to maintain oxygen-free conditions. For instance, pertechnetate solutions may contain dissolved oxygen which, if not detected prior to combination with the pertechnetate reducing agent, forms a product which is unstable and results in the undesirable formation of free pertechnetate-99m.

Others have disclosed means for overcoming the aforesaid instability problem using chemical stabilizers. German Offenlegungsschrift No. 2,618,337, Tofe, published Nov. 11, 1976, discloses the use of ascorbate stabilizers with technetium scanning agents. U.S. Pat. No. 4,075,314, issued Feb. 21, 1978, discloses the use of ascorbate to inhibit the oxidation of $Sn^{+2}$ and to inhibit the reoxidation of reduced technetium in a pyrophosphate-based bone scanning agent.

It has now been discovered that gentisate compounds are safe, effective, and non-interfering stabilizers for scanning agents used in the radiographic diagnosis of tissues (including bone mineral) of humans and lower animals.

SUMMARY OF THE INVENTION

Materials which are useful stabilizers for radiodiagnostic agents must exhibit the following properties:
(1) Toxicological acceptability under the conditions of use;
(2) The ability to stabilize the product for a reasonable period of storage and/or under use conditions; and
(3) No substantial interference with the delivery of the radionuclide to the intended organ.

The present invention is based on the discovery that the "gentisates", i.e., gentisic acid and its water-soluble salts and esters, stabilize radiodiagnostic agents without interfering with the ability of such agents to target specific organs. When used in the manner disclosed herein, the gentisates meet all of the above three criteria for a stabilizer.

The present invention provides highly stable compositions useful in the preparation of technetium-99m-based scintigraphic scanning agents. The compositions of the present invention comprise a pertechnetate reducing agent or oxidized pertechnetate solution and an effective amount, sufficient to stabilize said compositions in the presence of oxygen and radiolysis products, of gentisic acid or the water-soluble, pharmaceutically-acceptable salts or esters thereof.

In a preferred method aspect, the present invention encompasses an improved method of preparing a technetium-based scanning agent comprising codissolving gentisic acid, or the water-soluble, pharmaceutically-acceptable salts or esters thereof, and a pertechnetate reducing agent in an oxidized pertechnetate solution.

The stabilizing amount of gentisate stabilizer used in the practice of this invention is an amount which inhibits or reduces the oxidation of the pertechnetate reducing agent (e.g., oxidation of $Sn^{+2}$ to $Sn^{+4}$) during storage and/or inhibits or reduces the reoxidation of reduced technetium and/or formation of technetium labeled impurities during use.

All percentages and ratios herein are by weight, unless otherwise specified.

DETAILED DESCRIPTION OF THE INVENTION

This invention is based on the discovery that gentisic acid and its salts and esters (hereinafter "gentisates") can be utilized to prepare highly stable technetium-99m-based scintigraphic scanning agents. As known in the art, $^{99m}$Tc-labeled scanning agents are prepared by mixing a pertechnetate solution with a pertechnetate reducing agent. It has been found that small amounts of gentisic acid, its salts or esters, can be combined with either the pertechnetate solution or the pertechnetate reducing agent, thereby providing compositions uniquely suited for the preparation of superior, stable $^{99m}$Tc scanning agents.

There are several compositional aspects to the present invention. In one aspect, compositions of the present invention comprise a pertechnetate reducing agent which provides a pertechnetate reducing metal or cation, and the gentisate stabilizer. Such compositions comprise a stabilizing amount of the gentisate stabilizer. In a second aspect, the compositions of the present invention comprise a pertechnetate solution having dissolved therein a stabilizing amount of the gentisate stabilizer.

When practicing the present invention, it is not critical which compositional form is used to prepare the final technetium-based scanning agent. Commercial producers of pertechnetate generators may find it desirable to dissolve low levels of the gentisate stabilizer directly into the pertechnetate solution as it is eluted from the generator, or to incorporate a gentisate stabilizer directly on the generator column. Alternatively, it may be more convenient to combine the gentisate compound with the pertechnetate reducing agent. In either case, upon combining the pertechnetate solution with the reducing agent and gentisate stabilizer, an improved, highly stable scanning agent is provided.

Gentisate Stabilizer

Gentisic acid (chemically: 2,5-dihydroxybenzoic acid) is an article of commerce which can be prepared by several known methods, including oxidation of salicyclic acid with potassium persulfate (German Pat. No. 81,297), by heating hydroquinone and potassium bicarbonate in glycerol under a current of $CO_2$ (Ann. 351, 321, 1907) and by boiling hydroquinone with carbon tetrachloride and sodium hydroxide in the presence of copper (German Pat. No. 258,837).

The pharmaceutically-acceptable salts and esters of gentisic acid can be prepared by standard well-known neutralization and esterification procedures. A thorough discussion of suitable procedures for preparing salts and esters of carboxylic acids can be found in *The Chemistry of Organic Compounds*, Third; Noller (Ed.) 1966. In general, the pharmaceutically-acceptable salts of gentisic acid can be prepared by acid-base neutralization using a base which is selected to provide a water-soluble reaction product having a pharmaceutically-acceptable counter ion. Similarly, the pharmaceutically-acceptable esters of gentisic acid (esterified at the carboxyl moiety) can be prepared by reacting equimolar amounts of the acid with selected alcohols. Gentisic acid can also be esterified at one or both of its hydroxyl groups by reaction with an acid halide. Various salts, esters and derivatives of gentisic acid are known in the literature.

In practice, the salts and esters of gentisic acid suitable for use in the present invention can be selected according to their solubility in a pertechnetate solution. It is, of course, preferable that the salts and esters of gentisic acid be readily soluble in a pertechnetate solution. Accordingly, suitable gentisic acid salts include the soluble alkali metal, alkaline earth metal, heavy metal and ammonium salts. The alkali metal salts such as sodium (preferred), potassium and lithium salts of gentisic acid are readily soluble and accordingly quite useful herein. Sodium gentisate is available as the 5.5 hydrate; it retains 0.5 hydrate tenaciously; it is available under trademarks such as Gentinatre, Gentisod and Legential and is used as an analgesic and diaphoretic, in much the same manner as the salicylates.

Various gentisic acid ammonium salts, wherein the cation is $N(R')_4$ are also suitable for use herein. These include, for example, alkylammonium, alkanolammonium and arylammonium salts of gentisic acid. It is of course understood that the solubility of ammonium salts is largely dependent upon the number and nature of the substituent groups on the nitrogen atom. In general, and as used herein, preferred readily soluble gentisate ammonium salts include those wherein each R' is either hydrogen or $C_1$ to about $C_5$ hydrocarbyl. Non-limiting examples of pharmaceutically-acceptable ammonium salts of gentisic acid useful herein include the ammonium, methylammonium, dimethylammonium, tetramethylammonium, bis-(tetramethylammonium), 2-hydroxypropylammonium, bis-(2-hydroxypropylammonium), ethanolammonium, diethanolammonium, triethanolammonium, bis-(triethanolammonium), phenylammonium, naphthylammonium and quinolylammonium salts.

The alkaline earth metal gentisate salts, for example the calcium and magnesium salts, which, although less soluble, are also suitable for use herein.

The heavy metal salts, for example the iron (ferrous and ferric) and tin (stannous) salts, are also suitable for use herein. The stannous salt and ferrous salt are especially useful, inasmuch as these compounds each provide both the reducing agent for the technetium ($Sn^{+2}$ or $Fe^{+2}$) and the gentisate ion stabilizer.

The pharmaceutically-acceptable esters of gentisic acid (esterified at the carboxyl group of gentisic acid) which are sufficiently soluble in pertechnetate solutions include, for example, the $C_1$ to $C_5$ lower alkyl esters such as the methyl, ethyl, propyl, isopropyl, butyl, isobutyl and pentyl esters of gentisic acid.

Soluble gentisates esterified at the hydroxyl group also include the 2, the 5, and the 2,5-alkyl ($C_1$-$C_5$) esters. These are somewhat less effective stabilizers than the other gentisates.

Reducing Agent

In embodiments of this invention in which the gentisic acid compound is combined with the pertechnetate reducing agent, the choice of reducing agent is not critical. As used herein the term "pertechnetate reducing agent" is intended to include compounds, complexes, or the like, comprising a reducing ion capable of reducing heptavalent technetium ($TcO_4^-$) to trivalent, tetravalent and/or pentavalent technetium. Free metals such as tin are also known for use as pertechnetate reducing agents, although undissolved metal must be removed from the scanning solution prior to injection into the patient. Thus, it is more convenient to use metal compounds which provide the reducing metal cation in soluble form.

Suitable pertechnetate reducing agents can be combined with numerous adjuvants such as fillers and skeletal- or other organ-specific carriers. As disclosed by Tofe and Francis, and Tofe, et al., above, skeletal scanning agents have been prepared utilizing metallic salts of sulfuric and hydrochloric acid such as stannous chloride, chromous chloride and ferrous sulfate as the pertechnetate reducing agent in combination with various organic phosphonates and/or phosphates as the bone seeking carrier. Other systems capable of reducing pertechnetate-99m include, for example, acid-thiosulfates, acid-hydrogen-sulfates, iron colloids, and acid-borohydrides. U.S. Pat. Nos. 3,735,001 granted May 22, 1973; 3,863,004 granted Jan. 28, 1975; 3,466,361 granted Sept. 9, 1969; 3,720,761 granted Mar. 13, 1973; 3,723,612 granted Mar. 27, 1973; 3,725,295 granted Apr. 3, 1973; 3,803,299 granted Apr. 9, 1974; and 3,749,556 granted July 31, 1973 (all incorporated herein by reference) disclose various pertechnetate reducing agents comprising reducing ions capable of reducing heptavalent pertechnetate to appropriate lower valence states.

The amount of the gentisate stabilizer utilized in embodiments of this invention in which the gentisate is combined with a reducing agent will vary depending on the ultimate use of the composition and the amount of inert or filler materials utilized. Too much gentisate can cause excess soft tissue uptake and can interfere with organ (especially bone) imaging. In general, the weight ratio of gentisate stabilizer:reducing agent in a gentisate-plus-reducing agent composition is in the range of about 20:1 to about 1:20, preferably about 10:1 to about 1:1, more preferably about 5:1 to 1:1, most preferably about 3:1.

Where it is desirable to incorporate the gentisate stabilizer directly into the pertechnetate solution, the soluble gentisate compound can be simply dissolved either during or after elution of the pertechnetate source. The elution process is thoroughly described in U.S. Pat. No. 3,369,121 (incorporated herein by reference).

In embodiments of the present invention in which the gentisate stabilizer is dissolved in a pertechnetate solution, the concentration of gentisate will vary somewhat depending upon the degree of aqueous dilution. With current commercial pertechnetate sources, a concentration of gentisate no greater than about 0.1%, preferably no greater than 0.05%, by weight, provides adequate stability and does not interfere with organ distribution of the scanning agent. A concentration within the range of from about 0.0005% to about 0.05% is quite acceptable for many applications.

The present invention also encompasses an improved method of preparing technetium-based scanning agents comprising codissolving a gentisate stabilizer and a pertechnetate reducing agent in an aqueous pertechnetate solution. As described above, the gentisate compound and pertechnetate reducing agent can be either simultaneously dissolved or sequentially dissolved in the pertechnetate solution. Either codissolving procedure results in an improved technetium-based scanning agent.

Scanning agents also typically employ carrier agents which direct, or "target", the radionuclide to the desired organ. Broadly speaking, there are two classes of such carrier agents: those which target soft tissue organs such as the heart, marrow, liver, spleen, kidneys and lungs; and those which target calcified tissue, such as bone and other tissues which may be undergoing pathological calcification. Examples of such carrier, or "targeting", agents for soft tissues include: colloidal sulfur, albumin, and the like. Targeting agents for bone mineral include the water-soluble phosphates and (preferably) phosphonates.

For purposes of the present invention a normal physiologically-acceptable pH of from about 3 to 8, preferably 4 to about 6, is used in the preparation of the scanning agent.

In a preferred and convenient embodiment of the present invention, a stable technetium-based skeletal scanning agent can be formed by the direct addition of an aqueous, radioactive pertechnetate solution to a composition comprising: an amount of a pertechnetate reducing agent containing a metallic reducing ion in water-soluble form, such as stannous chloride, sufficient to reduce said pertechnetate; an amount of a water-soluble gentisate compound sufficient to stabilize the skeletal scanning agent; and an amount of a skeletal-specific carrier compound selected from the mono-, di- or polyphosphonates sufficient to carry the radioactive technetium to bone. The radio of reducing agent: phosphonate:gentisate can be adjusted to provide skeletal uptake with sufficiently low soft tissue uptake that scan quality is not undesirably affected.

A broad range of mono-, di- and polyphosphonates are now known to concentrate on the skeleton upon injection of solutions thereof into a patient. These phosphonates serve to "target" the radioactive technetium to the bone mineral. Operable species for this purpose include mono-, di- and polyphosphonates selected from the group consisting of:

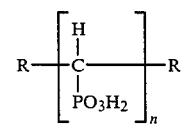

I.

wherein each R is hydrogen or $CH_2OH$ and n is an integer of from 3 to 10;

II.

wherein $R_1$ is hydrogen, alkyl containing from 1 to about 20 carbon atoms, alkenyl containing from 2 to about 20 carbon atoms, aryl (e.g., phenyl, naphthyl), phenylethenyl, benzyl, halogen (e.g., chlorine, bromine and fluorine), hydroxyl, amino, substituted amino (e.g., dimethylamino, diethylamino, N-hydroxy-N-ethylamino, acetylamino), —$CH_2COOH$, —$CH_2PO_3H_2$, $CH(PO_3H_2)(OH)$, or —$[CH_2C(PO_3H_2)_2]_n$—H where n=1 to 15, $R_2$ is hydrogen, lower alkyl (e.g., methyl, ethyl, propyl and butyl), amino, benzyl, halogen (e.g., chlorine, bromine, and fluorine), hydroxyl, —$CH_2COOH$, —$CH_2PO_3H_2$, or —$CH_2CH_2PO_3H_2$;

$$\text{III.} \quad \underset{\displaystyle (CH_2)_n}{\boxed{\phantom{xx}}} \underset{\displaystyle CH}{-} \underset{\displaystyle \underset{PO_3H_2}{|}}{\overset{\displaystyle \overset{PO_3H_2}{|}}{C}} -OH$$

wherein n is an integer of from 3 to 9;

$$\text{IV.} \quad R_3-\underset{\displaystyle \underset{R_3}{|}}{\overset{\displaystyle \overset{PO_3H_2}{|}}{C}}-R_3 \\ \underset{\displaystyle H_2O_3P-\underset{\displaystyle \underset{R_3}{|}}{C}}{\overset{R_3}{\diagdown}} \underset{\displaystyle N}{\phantom{x}} \overset{\displaystyle \diagup R_3}{\phantom{x}} \underset{\displaystyle \underset{R_3}{|}}{C}-PO_3H_2$$

wherein each $R_3$ is hydrogen or lower alkyl (e.g., methyl, ethyl, propyl and butyl);

$$\text{V.} \quad \underset{\displaystyle (CF_2)_n}{\boxed{\phantom{xx}}} \underset{\displaystyle \Vert}{\overset{\displaystyle C-PO_3H_2}{\phantom{x}}} \\ \phantom{xxxxxx} C-PO_3H_2$$

wherein n is an integer of from 2 to 4;

$$\text{VI.} \quad \begin{array}{c} O \\ \Vert \\ OH-P-OH \quad O \\ | \quad\quad\quad \Vert \\ C-O-P-OH \\ | \quad\quad | \\ OH-P\phantom{xx}O\phantom{xx}C \\ \Vert \quad\quad\quad | \\ O \quad OH-P-OH \\ \phantom{xxxxxx} \Vert \\ \phantom{xxxxxx} O \end{array}$$

$$\text{VII.} \quad \begin{array}{cc} COOH & COOH \\ | & | \\ C\!=\!\!=\!\!=\!\!C \\ | & | \\ H & PO_3H_2 \end{array}$$

$$\text{VIII.} \quad \begin{array}{cc} H & O \\ | & \diagup\!\!\Vert \\ H-C\!\!-\!\!-\!\!-\!\!-\!\!-\!\!C \\ | & | \\ O\!=\!P-OH & O\!=\!P-OH \\ | & | \\ OH & OH \end{array}$$

$$\text{IX.} \quad \begin{array}{cc} & OH \\ & | \\ H & O\!=\!P-OH \\ | & | \\ C\!=\!\!=\!\!=\!\!C \\ | & | \\ H & O\!=\!P-OH \\ & | \\ & OH \end{array}$$

$$\text{X.} \quad \begin{array}{cc} COOH & COOH \\ | & | \\ X-C\!\!-\!\!-\!\!-\!\!-\!\!-\!\!C-Y \\ | & | \\ PO_3H_2 & PO_3H_2 \end{array}$$

wherein X and Y are each hydrogen or hydroxy; and the non-toxic salts of each of the foregoing phosphonates which in an essentially neutral aqueous solution will react with hereinafter enumerated reducing/complexing materials; i.e., stannous, ferrous, or chromous salts to form the corresponding stannous, ferrous or chromous phosphonate salt. Suitable reactive phosphonate salts (hereinafter referred to as pharmaceutically acceptable salts) for use with the present invention include sodium, potassium, ammonium and low molecular weight substituted ammonium (e.g., mono-, di- and triethanolamine and quaternary ammonium) salts of the above phosphonates and mixtures thereof.

Operable polyphosphonates of the above formula (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid; nonane-1,2,3,4,5,6,7,8,9-nonaphosphonic acid; decane-1,2,3,4,5,6,7,8,9,10-decaphosphonic acid; and the pharmaceutically acceptable salts of these acids, e.g., sodium, potassium, ammonium, triethanolammonium, diethanolammonium, and monoethanolammonium salts.

Propane-1,2,3-triphosphonic acid and salts thereof can be prepared by a process disclosed in the copending application of D. A. Nicholson and D. Campbell, Ser. No. 82,819, filed Oct. 21, 1970, now U.S. Pat. No. 3,743,688.

Butane-1,2,3,4-tetraphosphonic acid and salts thereof can be prepared by a process disclosed in the copending application of D. A. Nicholson and D. Campbell, Ser. No. 67,200, filed Aug. 26, 1970, now U.S. Pat. No. 3,755,504.

The higher aliphatic vicinal polyphosphonates and salts thereof can be prepared by the process disclosed in U.S. Pat. No. 3,584,035 granted June 8, 1971.

Among the operable polyphosphonates encompassed by the above formula (II) are ethane-1-hydroxy-1,1-diphosphonic acid; methanediphosphonic acid; methanehydroxydiphosphonic acid; ethane-1,1,2,-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid; nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphono-prop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-dihydroxyethyl)-aminomethanediphosphonic acid; N-acetylaminomethanediphosphonic acid; aminomethanediphosphonic acid; dihydroxymethanediphosphonic acid; and the pharmaceutically acceptable salts of these acids, e.g., sodium, potassium, ammonium, triethanolammonium, diethanolammonium, and monoethanolammonium salts.

Ethane-1-hydroxy-1,1-diphosphonic acid, an especially preferred polyphosphonate, has the molecular formula $CH_3C(OH)(PO_3H_2)_2$. (According to nomenclature by radicals, the acid might also be named 1-hydroxyethylidene diphosphonic acid.)

While any pharmaceutically acceptable salt of ethane-1-hydroxy-1,1-diphosphonic acid can be used in the practice of this invention, mixtures of the disodium and trisodium salts are most preferred. The other sodium, potassium, ammonium, and mono-, di-, and triethanolammonium salts and mixtures thereof are also suitable, provided caution is observed in regulating the total intake of cation species in the salt composition. These compounds can be prepared by any suitable method; however, an especially preferred method is disclosed in U.S. Pat. No. 3,400,149 granted Sept. 3, 1968.

Methanehydroxydiphosphonic acid and related compounds operable herein can be prepared, for example, by reaction of phosgene with an alkali metal dialkylphosphite. A complete description of these compounds and a method for preparing same is found in U.S. Pat. No. 3,422,137 granted Jan. 14, 1969.

Methanedihydroxydiphosphonic acid and salts useful herein and a method for preparing same are disclosed in U.S. Pat. No. 3,497,313 granted Feb. 24, 1970.

Methanediphosphonic acid and related compounds useful herein are described in detail in U.S. Pat. No. 3,213,030, granted Oct. 19, 1965. A preferred method of preparing such compounds is disclosed in U.S. Pat. No. 3,251,907 granted May 17, 1966.

Ethane-1,1,2-triphosphonic acid and related compounds which can be used in the compositions of this invention, as well as a method for their preparation, are fully described in U.S. Pat. No. 3,551,339 granted Dec. 29, 1970.

Propane-1,1,3,3-tetraphosphonic acid and related compounds useful herein, and a method for preparing same, are fully disclosed in U.S. Pat. No. 3,400,176 granted Sept. 3, 1968. The higher methylene interrupted methylene diphosphonate polymers can be prepared by the polymerization of ethylene-1,1-diphosphonate.

Pentane-2,2-diphosphonic acid and related compounds can be prepared in accordance with the method described by G. M. Kosolopoff in *J. Amer. Chem. Soc.*, 75, 1500 (1953).

Operable phosphonates of formula (III) above include the following:
Methanecyclobutylhydroxydiphosphonic acid
Methanecyclopentylhydroxydiphosphonic acid
Methanecyclohexylhydroxydiphosphonic acid
Methanecycloheptylhydroxydiphosphonic acid
Methanecyclooctylhydroxydiphosphonic acid
Methanecyclononylhydroxydiphosphonic acid
Methanecyclodecylhydroxydiphosphonic acid.

Each of the sodium, potassium, ammonium, monoethanolammonium, diethanolammonium, and triethanolammonium salts of the above-recited methanecycloalkylhydroxydiphosphonic acids as well as any other pharmaceutically acceptable salt of these acids, also selectively seek the skeleton.

The phosphonates of formula (III) can be prepared by methods fully described in U.S. Pat. No. 3,584,125, granted June 8, 1971.

The preferred phosphonates of formula (IV) for the purpose of this invention are tris(phosphonomethyl)amine; tris(1-phosphonoethyl)amine; tris(2-phosphono-2-propyl)amine; and their pharmaceutically acceptable salts. Tris(phosphonomethyl)amine is especially preferred. The following are exemplary of compounds which can also be used:

(a) bis(phosphonomethyl)-1-phosphonoethyl amine;
(b) bis(phosphonomethyl)-2-phosphono-2-propyl amine;
(c) bis(1-phosphonoethyl)phosphonomethyl amine;
(d) bis(2-phosphono-2-propyl)phosphonomethyl amine;
(e) tris(1-phosphono-1-pentyl)amine;
(f) bis(phosphonomethyl)2-phosphono-2-hexyl amine; and
(g) the pharmaceutically acceptable salts of acids (a) through (f), e.g., sodium, potassium, ammonium, triethanolammonium, diethanolammonium, and monoethanolammonium salts.

The tris(phosphonoalkyl)amines can be prepared, for example, by first preparing the corresponding ester in accordance with the general reaction:

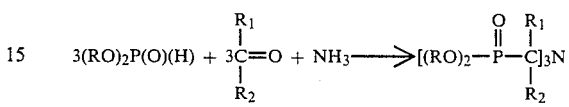

wherein R is alkyl and $R_1$ and $R_2$ are hydrogen or lower alkyl.

The free acids can be prepared by hydrolysis of the ester using strong mineral acids such as hydrochloric acid. The salts are, of course, prepared by neutralizing the acid with the base of the desired cation. The preparation of tris(phosphonoalkyl)amines is fully disclosed by Irani. et al., in Canadian Pat. No. 753,207, issued Feb. 21, 1967.

The phosphonates of formula (V) include the following: (1) 3,3,4,4,5,5-hexafluoro-1,2-diphosphonocyclpent-1-ene; (2) 3,3,4,4-tetrafluoro-1,2-diphosphoncyclobut-1-ene; and (3) 3,3,4,4,5,5,6,6-octafluoro-1,2-diphosphonocyclohex-1-ene.

The perfluorodiphosphonocycloalkenes can be prepared, for example, by reacting trialkyl phosphites with 1,2-dichloroperfluorocycloalk-1-enes in accordance with the procedures fully described by Frank in *J. Org. Chem.* 31, #5, p. 1521.

The phosphonate of formula (VI) is referred to herein as cyclic tetraphosphonic acid. This compound and its pharmaceutically acceptable salts can be prepared by any suitable method; however, an especially preferred method is disclosed by Oscar T. Quimby, U.S. Pat. No. 3,387,024 granted June 4, 1968.

Operable phosphonates encompassed by the above formula (VII) are ethene-1,2-dicarboxy-1-phosphonic acid; and the pharmaceutically acceptable salts of these acids, e.g., sodium, potassium, ammonium, triethanolammonium, diethanolammonium, and monoethanolammonium salts. While the above formula (VII) is representative of cis-isomers, the corresponding trans-isomers are also useful herein. Reference hereinafter to ethene-1,2-dicarboxy-1-phosphonic acid or salts thereof, unless otherwise specified, is intended as contemplating the cis- and trans-isomers and mixtures thereof.

Ethene-1,2-dicarboxy-1-phosphonic acid and related compounds useful herein can be prepared by reaction of an ester of acetylenedicarboxylic acid and a dialkyl phosphite followed by hydrolysis and saponification. This method is more fully described in U.S. Pat. No. 3,584,124, granted June 8, 1971.

The sodium salt of formula (VIII) can be made by the rearrangement reaction of a 2-haloethane-1-hydroxy-1,1-diphosphonic acid with about 3 equivalents of sodium hydroxide as disclosed in U.S. Pat. No. 3,641,126.

The phosphonate of formula (IX) can be made by the method of German Offenlegungsschrift No. 2,026,078.

Operable carboxyphosphonates of the above formula (X) include ethane-1,2-dicarboxy-1,2-diphosphonic acid; ethane-1,2-dicarboxy-1,2-dihydroxy-1,2-diphosphonic acid; ethane-1,2-dicarboxy-1-hydroxy-1,2-diphosphonic acid; and the pharmaceutically acceptable salts of these acids, e.g., sodium, potassium, ammonium, triethanolammonium, diethanolammonium and monoethanolammonium salts.

Ethane-1,2-dicarboxy-1,2-diphosphonic acid, a preferred carboxyphosphonate herein, has the molecular formula $CH(COOH)(PO_3H_2)CH(COOH)(PO_3H_2)$. The most convenient crystallizable salts of this acid are obtained when three, four or five of the acid hydrogens are replaced by sodium.

While any pharmaceutically acceptable salt of ethane-1,2-dicarboxy-1,2-diphosphonic acid can be used in the practice of this invention, the tetrasodium dihydrogen salt, the trisodium trihydrogen salt, the disodium tetrahydrogen salt, the monosodium pentahydrogen salt, and the mixtures thereof are useful. The other potassium, ammonium, and mono-, di-, and triethanolammonium, etc., salts and mixtures thereof are also suitable, provided caution is observed in regulating the total intake of cation species in the salt composition.

Ethane-1,2-dicarboxy-1,2-diphosphonic acid and suitable salts thereof can be prepared in any convenient manner. For example, the reaction described by Pudovik in "Soviet Research on Organo-Phosphorus Compounds", 1949–1956, Part III, 547-85c. can be used to prepare the ester of ethane-1,2-dicarboxy-1,2-diphosphonic acid which in turn can, by ordinary hydrolysis reactions, be converted to the free acid form. Neutralization by alkali compounds such as sodium hydroxide, potassium hydroxide, carbonates and the like can be used to prepare a desired salt of the acid. A more detailed description of the preparation of these compounds is described in U.S. Pat. No. 3,562,166 granted Feb. 9, 1971.

Ethane-1,1-dicarboxy-1,2-dihydroxy-1,2-diphosphonic acid and related compounds useful herein can be prepared by reaction of an ester of ethane-1,2-dicarboxy-1,2-diphosphonic acid and an alkali metal hypohalite followed by hydrolysis and saponification. This method is more fully described in U.S. Pat. No. 3,579,570 granted May 18, 1971.

Mixtures of any of the foregoing phosphonic acids and/or salts can be used in the practice of this invention.

In a highly preferred embodiment of this invention, mixtures of disodium- and trisodium-ethane-1-hydroxy-1,1-diphosphonate salts wherein the mole ratio of the disodium salt to trisodium is from about 4:1 to 1:1, more preferably 3:1 to 1:1, are employed in the pertechnetate reducing agent along with a gentisate stabilizer and a reducing metallic ion. These preferred phosphonate/reducing ion/gentisate mixtures provide especially good scintiscans, with excellent stability and skeletal uptake and little soft tissue uptake.

The aminophosphonates, especially the aminopropane diphosphonates disclosed in U.S. Pat. Nos. 4,054,598 and 3,962,432 (incorporated herein by reference) are also useful in preparing bone scanning agents stabilized with gentisates.

The following examples are illustrative of compositions made according to this invention. The quantity of each component listed is in milligrams.

| COMPONENT | I | II | III | IV | V | VI | VII | VIII | IX | X |
|---|---|---|---|---|---|---|---|---|---|---|
| Disodium-ethane-1-hydroxy-1,1-diphosphonate | 5.9 | | 5.9 | 5.9 | 5.9 | | | | 4 | 3 |
| Trisodium-ethane-1-hydroxy-1,1-diphosphonate | | 5.9 | | | | | | | 1.9 | |
| Disodium-methane-diphosphonate | | | | | | | | 5.9 | | |
| Trisodium-methane-diphosphonate | | | | | | | 5.9 | | | 2.9 |
| Dichloromethanediphosphonic acid | | | | | | 5.9 | | | | |
| Stannous chloride | 0.16 | 0.16 | | | 0.16 | | 0.16 | | | 0.16 |
| Ferrous sulfate | | | 0.16 | | | 0.16 | | 0.16 | | |
| Chromous chloride | | | | 0.16 | | | | | 0.16 | |
| Sodium chloride | 27 | | 27 | | 27 | | 27 | | 27 | 27 |
| Glucose | | 27 | | 27 | | 27 | | | | |
| Sodium gentisate | 0.5 | | | | 0.5 | | | | 0.5 | 0.5 |
| Gentisic acid | | 0.5 | | | | | 0.5 | | | |
| Methyl gentisate | | | | 0.7 | | | | | 0.7 | |
| Diethanolammonium gentisate | | | | | | 0.5 | | | | |

Each of the compositions of Examples I through X, upon addition of about 5 ml. of a pertechnetate-99m solution from a commercial technetium source, and thorough shaking, yields a skeletal scanning agent suitable for intravenous injection into a human patient. The in-use stability of such skeletal scanning agents is more than three hours, which is ample under ordinary hospital conditions. Preferably, about 1 ml. of the skeletal scanning solution is used in an adult of about 50–100 kilograms body weight and is injected slowly, over a period of about 30 seconds. Administration is preferably done within about three hours of preparation. Kits can, of course, contain multiples or fractions of the above amounts to allow preparation of sufficient agent from a single vial to perform any desired number of scans.

The following example is illustrative of a pertechnetate solution having dissolved therein a gentisate stabilizer.

EXAMPLE XI

A collecting vial containing 0.1 mg. of sodium gentisate is placed at the elute orifice of a pertechnetate-99m generator. Saline elute is collected in the vial and completely dissolves the sodium gentisate.

Approximately 5 ml. of the pertechnetate solution, with dissolved sodium gentisate, is added to a pertechnetate reducing agent comprising 5.9 mg. of the sodium salt of ethane-1-hydroxy-1,1-diphosphonic acid and 0.16 mg. of stannous chloride. Afterthorough shaking, a stable bone scanning agent suitable for intravenous injection into a human patient is prepared.

In the above example, sodium gentisate is replaced by equivalent amounts of gentisic acid, methyl gentisate, ethyl gentisate, diethanolamine gentisate, calcium gentisate, magnesium gentisate, potassium gentisate, and tetramethylammonium gentisate, and stable scanning agents are prepared.

The use of methanehydroxydiphosphonate (MHDP) as a highly preferred bone scanning agent which provides exceptionally sharp scintiphotos and excellent lesion detection is described in the copending application of Bevan, Ser. No. 929,472, filed July 31, 1978, now U.S. Pat. No. 4,247,534 entitled RADIOGRAPHIC SCANNING AGENT. The following example illustrates the preparation of a freeze-dried product containing MHDP as the bone-seeking agent.

EXAMPLE XII

Methanehydroxydiphosphonate, mixture of di-, and tri-sodium salts (2.0 mg.), stannous chloride (0.16 mg.), and gentisic acid (0.50 mg.) are dissolved in 1 ml. of deoxygenated water at room temperature. The aqueous solution is filtered through a millipore filter and freeze-dried on a commercial apparatus.

The freeze-dried powder prepared in the foregoing manner is admixed with about 5 ml. of a pertechnetate-99m solution from a commercial source. The freeze-dried powder dissolves readily and a stable skeletal scanning agent suitable for intravenous use is secured.

The foregoing examples have illustrated the use of gentisates in the preparation of scanning agents using various phosphonate materials to target bone mineral. Inorganic phosphates are also useful in the manufacture of bone scanning agents and radiodiagnostic products containing inorganic phosphates can also be stabilized with the gentisates herein.

U.S. Pat. No. 4,016,249, issued Apr. 5, 1977, the disclosures of which are incorporated herein by reference, contains a succinct disclosure of the use of inorganic phosphates of various types in the manufacture of bone scanning agents. In particular, certain soluble pyrophosphate species having a molecular weight of less than about 300, said pyrophosphate containing no more than about 25% branched-chain polyphosphate, are quite useful for bone scanning. As with the organophosphonates, the pyrophosphate is conveniently used by admixture with a reducing salt for pertechnetate, thereby providing a kit. In use, the kit is charged with an aqueous solution of pertechnetate, whereupon the heptavalent technetium is reduced to a lower oxidation state, where it combines with the pyrophosphate. When injected into the patient the pyrophosphate targets bone mineral with the technetium radionuclide, in the manner of the organophosphonates. An example of such a product is as follows.

EXAMPLE XIII

| Ingredient | Amount (mg.) |
| --- | --- |
| Sodium gentisate | 0.20 |
| Stannous chloride | 1.30 |
| Sodium pyrophosphate* | 40.0 |

*As disclosed in U.S. Pat. No. 4,016,249.

The composition of Example XIII is prepared by simple admixture of the listed ingredients and used in the manner disclosed above.

In an alternate mode, the composition of Example XIII is prepared by dissolving the ingredients in water (20 ml.), sterilizing by filtration and freeze-drying using standard equipment.

Highly preferred, gentisate-stabilized bone scanning agents are as follows.

EXAMPLE XIV

| Ingredient | Milligrams/vial |
| --- | --- |
| EHDP* | 5.9 |
| $SnCl_2$ | 0.16 |
| Gentisic acid | 0.50 |
| NaCl | 26.5 |

*Mixture of di- and tri-sodium salts of ethane-1-hydroxy-1,1-diphosphonic acid

The ingredients are dry mixed. Five mls. of eluate from a commercial pertechnetate source added to one vial of the composition of Example XIV provides sufficient solution for 5 bone scans.

The composition of Example XIV is modified by replacing the EHDP with an equal amount of 3-amino-1-hydroxypropane-1,1-diphosphonic acid and a stabilized bone imaging agent is secured.

EXAMPLE XV

| Ingredient | Milligrams/vial |
| --- | --- |
| MHDP* | 2.0 |
| $SnCl_2$ | 0.16 |
| Gentisic Acid | 0.50 |
| NaCl | 26.5 |

*Mixture of sodium salts of methanehydroxydiphosphonic acid.

The ingredients are dry mixed. Five mls. of eluate from a commercial pertechnetate source added to one vial of the composition of Example XV provides sufficient solution for 5 bone scans.

EXAMPLE XVI

Ethane-1-hydroxy-1,1-diphosphonate, mixture of di-, and trisodium salts (5.9 mg), stannous chloride (0.16 mg.), and gentisic acid (0.50 mg.) are dissolved in 1 ml. of deoxygenated water at room temperature. The aqueous solution is filtered through a millipore filter and freeze-dried on a commercial apparatus.

The freeze-dried powder prepared in the foregoing manner is admixed with about 5 ml. of a pertechnetate-99m solution from a commercial source. The freeze-dried powder dissolves readily and a stable skeletal scanning agent suitable for intravenous use is secured.

In an alternate mode, stannous gentisate, ferrous gentisate and chromous gentisate are prepared by admixing stoichiometric amounts of gentisic acid and the respective metal halides in oxygen-free water, and the metal gentisate compounds are used as combined reducing/stabilizing agents in compositions of the foregoing type.

As can be seen from the foregoing, gentisate stabilizers provide excellent storage stability and in-use stability for $^{99m}Tc$-based scanning agents. When an organ-specific carrier such as an organophosphonate or inorganic phosphate is used in such compositions in the manner disclosed, it is preferred that the weight ratio of gentisate; carrier be in the range of from about 10:1 to about 1:30, preferably 1:1 to about 1:20, most preferably from about 1:5 to about 1:12.

As disclosed in the art, the weight ratio of reducing agent:carrier in such compositions is generally in the range 1:50 to about 1:20, although this ratio can vary with the type of organo-specific carrier being used. The gentisate stabilizer does not appreciably alter these ratios.

What is claimed is:
1. The water-soluble compound stannous gentisate.
2. The water-soluble compound chromous gentisate.

* * * * *